(12) United States Patent
Weisberg et al.

(10) Patent No.: US 8,688,610 B1
(45) Date of Patent: Apr. 1, 2014

(54) ESTIMATION OF INDIVIDUAL CAUSAL EFFECTS

(71) Applicant: Causalytics, LLC, Needham, MA (US)

(72) Inventors: Herbert I. Weisberg, Needham, MA (US); Victor P. Pontes, Stoneham, MA (US)

(73) Assignee: Causalytics, LLC, Needham, MA (US)

( * ) Notice: Subject to any disclaimer, the term of this patent is extended or adjusted under 35 U.S.C. 154(b) by 41 days.

(21) Appl. No.: 13/675,597

(22) Filed: Nov. 13, 2012

(51) Int. Cl.
*G06F 17/00* (2006.01)
*G06N 5/02* (2006.01)

(52) U.S. Cl.
USPC .......................................................... 706/46

(58) Field of Classification Search
None
See application file for complete search history.

(56) References Cited

U.S. PATENT DOCUMENTS

2004/0153249 A1* 8/2004 Zhang et al. ............... 702/19
2010/0278405 A1* 11/2010 Kakadiaris et al. ......... 382/131

OTHER PUBLICATIONS

Estimating Causal Effects George Maldonado and Sander Greenland.*
The central role of the propensity score in observational studies for causal effects by Paul R. Rosenbaum and Donald B. Rubin.*
Estimation of Causal Effects using Propensity Score Weighting: An Application to Data on Right Heart Catheterization Authors: Hirano K1; Imbens G.W.2.*
Propensity score methods in observational studies—estimating the marginal odds ratio Susanne Stampf.*
Alemi, F. et al., "Improved Statistical Methods are Needed to Advance Personalized Medicine," The Open Translational Medical Journal, 2009, vol. 1, pp. 16-20.
Cohen, J., "A Coefficient of Agreement for Nominal Scales," Educational and Psychological Measurement, 1960, vol. 20, pp. 37-46.
Freidin, B. et al., "Adaptive Signature Design: an Adaptive Clinical Trial Design for Generating and Prospectively Testing a Gene Expression Signature for Sensitive Patients," Clinical Cancer Research, Nov. 1, 2005, vol. 11, No. 21, pp. 7872-7878.
Freidin, B. et al., "The Cross-validated Adaptive Signature Design," Clinical Cancer Research, Jan. 15, 2010, vol. 16, No. 2, pp. 691-698.
Greenland, S. et al., "Identifiability, Exchangeability, and Epidemiological Confounding,"International Journal of Epidemiology, 1986, vol. 15, No. 3, pp. 413-419.
Hansotia, B. et al., "Direct Marketing for Multichannel Retailers: Issues, Challenges and Solutions,"Journal of Database Marketing, 2002, vol. 9, No. 3, pp. 259-266.
Jaskowski, M. et al., "Uplift modeling for clinical trial data," ICML 2012 Workshop on Clinical Data Analysis, Edinburgh, Scotland, UK, 2012, 8 pages.
Kravitz, R.L. et at., "Evidence-based Medicine, Heterogeneity of Treatment Effects, and the Trouble.with Averages," The Milbank Quarterly, 2004, vol. 82, No. 4, pp. 661-687.
Lo, V.S. "The True Lift Model—A Novel Data Mining Approach to Response Modeling in database Marketing," SIGKKD Explorations, 2002, vol. 4, No. 2, pp. 78-86.
Manahan, C. "A Proportional Hazards Approach to Campaign List Selection," SAS User Group International Proceedings, 2005, 30, 7 pages.

(Continued)

*Primary Examiner* — Kakali Chaki
*Assistant Examiner* — Ababacar Seck
(74) *Attorney, Agent, or Firm* — Foley & Lardner LLP

(57) ABSTRACT

Methods and media for facilitating estimation of the causal effect for individuals based on predictor factors associated with the individuals. Estimated values of the causal effect may be used to distinguish between individuals and to recommend treatment based on the predicted treatment effect for the individuals.

23 Claims, 7 Drawing Sheets

(56) References Cited

OTHER PUBLICATIONS

Radcliffe, N. J. et al., "Real-World Uplift Modelling with Significance-Based Uplift Trees," Portrait Technical Report TR-2011-1, Stochastic Solutions, 2011, 33 pages.

Ren, Z. et al., "Research Methods for Clinical Trials in Personalized Medicine: a Systematic Review," University of North Carolina at Chapel Hill Department of Biostatistics Technical Report Series, 2012, Paper 25, 41 pages.

Rosenbaum, P.R. et al., "The Central Role of the Propensity Score in Observational Studies for Causal Effects," Biometrika, 1983, vol. 70, No. 1, pp. 41-55.

Rubin, D.B., "Bayesian Inference for Causal Effects: the Role of Randomization," The Annals of Statistics, 1978, vol. 6, No. 1, pp. 34-58.

Rubin, D.B., "Estimating Causal Effects of Treatments in Randomized and Nonrandomized Studies," Journal of Educational Psychology, 1974, vol. 66, No. 5, pp. 688-701.

Rzepakowski, P. et al., "Decision Trees for Uplift Modeling with Single and Multiple Treatments," Knowledge and Information Systems, Aug. 2012, vol. 32, No. 2, pp. 303-327.

Rzepakowski, P. et al., "Decision Trees for Uplift Modeling," IEEE Conference on Data Mining, 2010, 10 pages.

Rzepakowski, P. et al., "Uplift Modeling in Direct Marketing," Journal of Telecommunications and Information Technology, 2012, vol. 2, pp. 43-50.

Simon, R., "The Use of Genomics in Clinical Trial Design," Clinical Cancer Research, Oct. 1, 2008, vol. 14, No. 19, pp. 5984-5993.

Weisberg, H.I. et al., "Selection Criteria and Generalizability Within the Counterfactual Framework: Explaining the Paradox of Antidepressant-Induced Suicidality?," Clinical Trials, 2009, vol. 6, pp. 109-118.

\* cited by examiner

ESTIMATION OF INDIVIDUAL CAUSAL EFFECTS

BACKGROUND

Any intervention in a system or process entails the possibility of gain or loss. For example, a company's new advertising campaign may increase, decrease, or have no effect on sales. As another example, a medical therapy may be effective, ineffective, or detrimental in treating a disease. To evaluate the efficacy of possible intervening "treatments," a scientist, analyst, marketer, or other investigator may apply the principles of statistical design of experiments. In particular, they may test alternative treatment modalities (often including a control or untreated modality) in two or more randomized groups. In some cases, the treatments may have a definite positive outcome (e.g., increased sales, cured disease, etc.). In such cases, different treatments are often evaluated by comparing the percentage of positive responses in each group, with the difference between the observed rates of response becoming the major determinant of which potential intervention will put into service. In other cases, the outcome of interest may be numerical in nature, such as the total dollars spent by a customer or the systolic blood pressure of a patient. In these "continuous" cases, the difference between the mean (average) values for the alternative treatment modalities is the usual measure of causal effect.

Traditional methods, therefore, produce an "average" estimate of causal effect presumed to be globally applicable. These methods are of very limited use in dealing with individual variability of the causal effect. They effectively assume that the causal effect is uniform across different individuals or, if it varies, that we are interested only in the average effect. If, instead, a researcher wishes to determine the causal effect for a single individual, then these traditional methods may prove ineffective.

One problem, recognized by the present inventors, in estimating a personalized treatment effect is that we can only observe each individual under a single treatment modality. For example, if a first medical treatment cures a person's disease, then there would be no reasonable way to test whether a second treatment would cure the person's disease. As another example, when a person is shown a first advertisement, the person may form such a lasting opinion about the subject of the advertisement that this opinion would alter the efficacy of any future advertisement. More generally, once a person receives a first treatment, they may not react to a second treatment in the same way as a person who initially receives the second treatment.

For every person, therefore, the outcome of only one treatment will ever be observed; while the other outcome (termed a "counterfactual" outcome) remains hidden. Statisticians are thus reduced to dealing with comparisons among groups of individuals. This basic conundrum makes the determination of an effect for each individual technically impossible.

SUMMARY

As will be shown, it is possible to estimate an effectively individual treatment effect, if certain potentially-predictive characteristics (variables) are assumed to be the primary sources of variability in the treatment effect. Disclosed herein are various methods and systems for helping to facilitate the determination and/or use of estimated treatment effects for individuals based on the predictor variables. Also disclosed are methods and systems for helping to determine which predictor variables are significant determinants of the individual causal effects. In order to facilitate such estimation, a special causality variable (termed herein the "cadit" or "cadit variable") will be defined.

In one embodiment, an example computer-implemented method involves receiving study data indicative of the exposure status, outcome, and predictor variables associated with participants in the study. The method further involves calculating a value of the cadit variable for each of several respective participants and analyzing the study data to estimate a statistical relationship between the value of the cadit and the predictor variables. Additionally, the method involves generating, based on the estimated statistical relationship, an algorithm for using values of the one or more predictor variables to distinguish between individuals according to an estimate of their individual causal effect (ICE).

In another embodiment, an example computer-implemented method for testing the statistical significance of one or more predictor variables for estimation of the ICE involves receiving study data indicative of the exposure status, study outcome, and predictor variables associated with participants in the study. The method further involves calculating a respective value of the cadit variable for each of several respective participants and performing a statistical analysis on the study data using the cadit as a dependent variable and the predictor variables as independent variables. Additionally, the method involves determining, based on the statistical analysis, the statistical significance of the predictor variables in relation to the cadit variable.

In a further embodiment, an example computer-readable medium contains program instructions that, when executed, cause a processor to perform various functions. The functions involve receiving study data indicative of the exposure status, study outcome, and predictor variables associated with participants in the study. The functions also involve calculating a value of the cadit variable for each of several respective participants and analyzing the study data to estimate a statistical relationship between the value of the cadit and the predictor variables. Further, the functions involve generating, based on the estimated statistical relationship, an algorithm for using values of the one or more predictor variables to distinguish between individuals according to an estimate of their individual causal effect (ICE).

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined by the claims, will become apparent in the detailed description set forth herein and taken in conjunction with the accompanying drawings.

DETAILED DESCRIPTION

I. Definitions

An individual causal effect ("ICE") will refer to the true causal effect for an individual who has certain characteristics.

The estimated causal effect ("ECE") for an individual is a statistical estimate of the ICE for the individual.

"Treatment" refers to any modality of intervention that may have an effect on individuals. Such a modality may be a specific interaction with an individual (e.g., medical treatment, advertisement, incentive, recommendation, etc.) or it may be a lack of interaction (e.g., administering a placebo, not showing an advertisement, etc.)

The terms "participant" and "individual" are used herein to describe any entity that may be affected by a treatment. For example, a participant may be a person, animal, plant, biological cell, organization, process, inanimate object, or business, among other examples.

"Expectation" is used herein to mean statistical expectation, which is the expected value of the variable based on the probability distribution of the variable.

II. Example System Architecture

Functions and procedures described herein may be executed according to any of several embodiments. For example, procedures may be performed by specialized equipment that is designed to perform the particular functions. As another example, the functions may be performed by general-use equipment that executes commands related to the procedures. As still another example, each function may be performed by a different piece of equipment with one piece of equipment serving as control or with a separate control device. As a further example, procedures may be specified as program instructions on a computer-readable medium.

Figure 1:
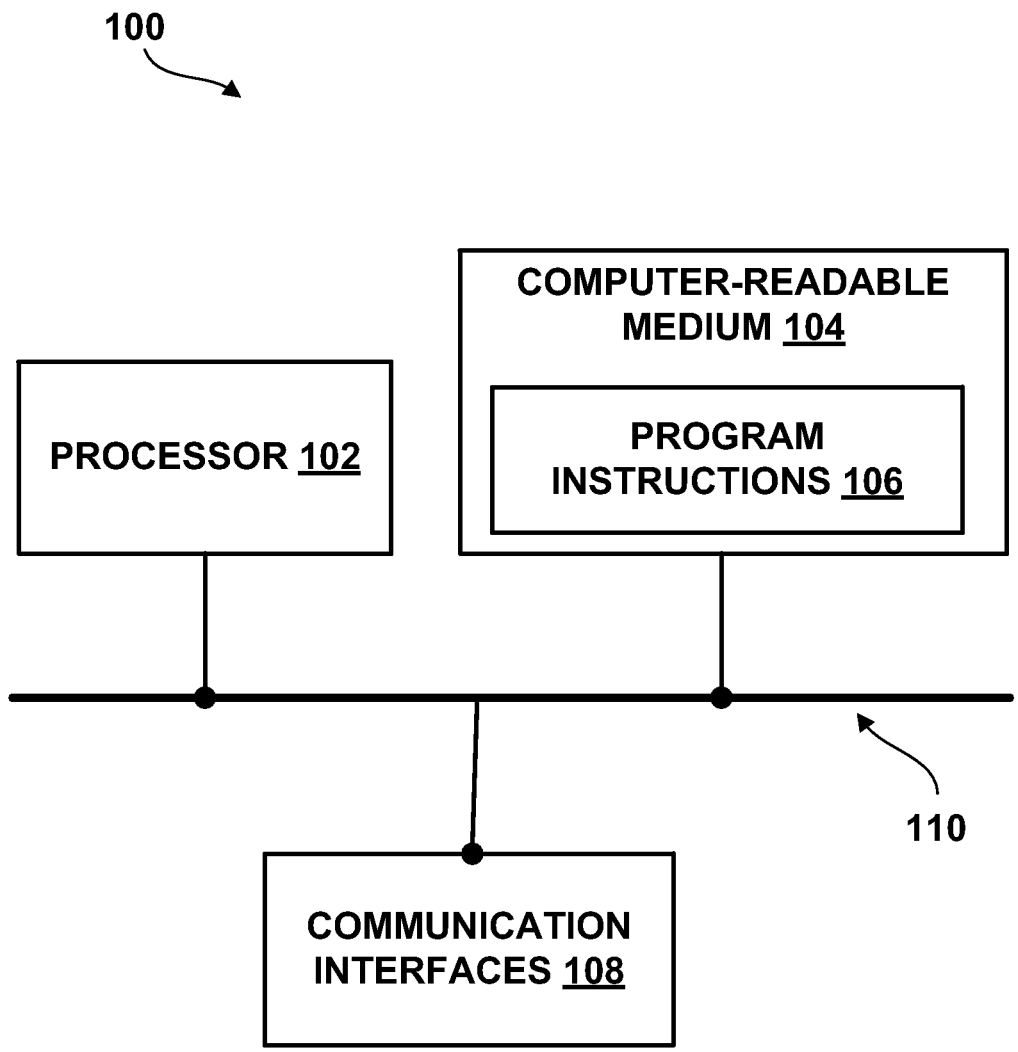
FIG. 1 is a schematic diagram of an example system for performing functions according to an exemplary embodiment.

One example system (100) is shown in FIG. 1. As shown, system 100 includes processor 102, computer-readable medium (CRM) 104, and communication interfaces 108, all connected through system bus 110. Also as shown, program instructions 106 are stored on computer-readable medium 104.

Processor 102 may include any processor type capable of executing program instructions 106 in order to perform the functions described herein. For example, processor 102 may be any general-purpose processor, specialized processing unit, or device containing processing elements. In some cases, multiple processing units may be connected and utilized in combination to perform the various functions of processor 102.

CRM 104 may be any available media that can be accessed by processor 102 and any other processing elements in system 100. By way of example, CRM 104 may include RAM, ROM, EPROM, EEPROM, CD-ROM or other optical disk storage, magnetic disk storage or other magnetic storage devices, or any other medium that can be used to carry or store desired program code in the form of program instructions or data structures, and which can be executed by a processor. When information is transferred or provided over a network or another communications connection (either hardwired, wireless, or a combination of hardwired or wireless) to a machine, the machine properly views the connection as a CRM. Thus, any such connection to a computing device or processor is properly termed a CRM. Combinations of the above are also included within the scope of computer-readable media.

Program instructions 106 may include, for example, instructions and data capable of causing a processing unit, a general-purpose computer, a special-purpose computer, special-purpose processing machines, or server systems to perform a certain function or group of functions.

Communication interfaces 108 may include, for example, wireless chipsets, antennas, wired ports, signal converters, communication protocols, and other hardware and software for interfacing with external systems. For example, system 100 may receive study data via communication interfaces 108 from remote data sources (e.g., remote servers, internet locations, intranet locations, wireless data networks, etc.) or from local media sources (e.g., external drives, memory cards, specialized input systems, wired port connections, wireless terminals, etc.) As another example, system 100 may receive user-input and user-commands via communication interfaces 108 such as, for instance, wireless/remote control signals, touch-screen input, actuation of buttons/switches, voice input, and other user-interface elements. Communication interfaces may also be used to output resulting data.

An example system may also include a variety of devices or elements other than those shown in FIG. 1. For example, system 100 may include visual displays or audio output devices to present results of an example process. As another example, CRM 104 may store computer applications for specific data-generation or data-processing functions. Other examples are possible.

III. Example Methods

Figure 2:
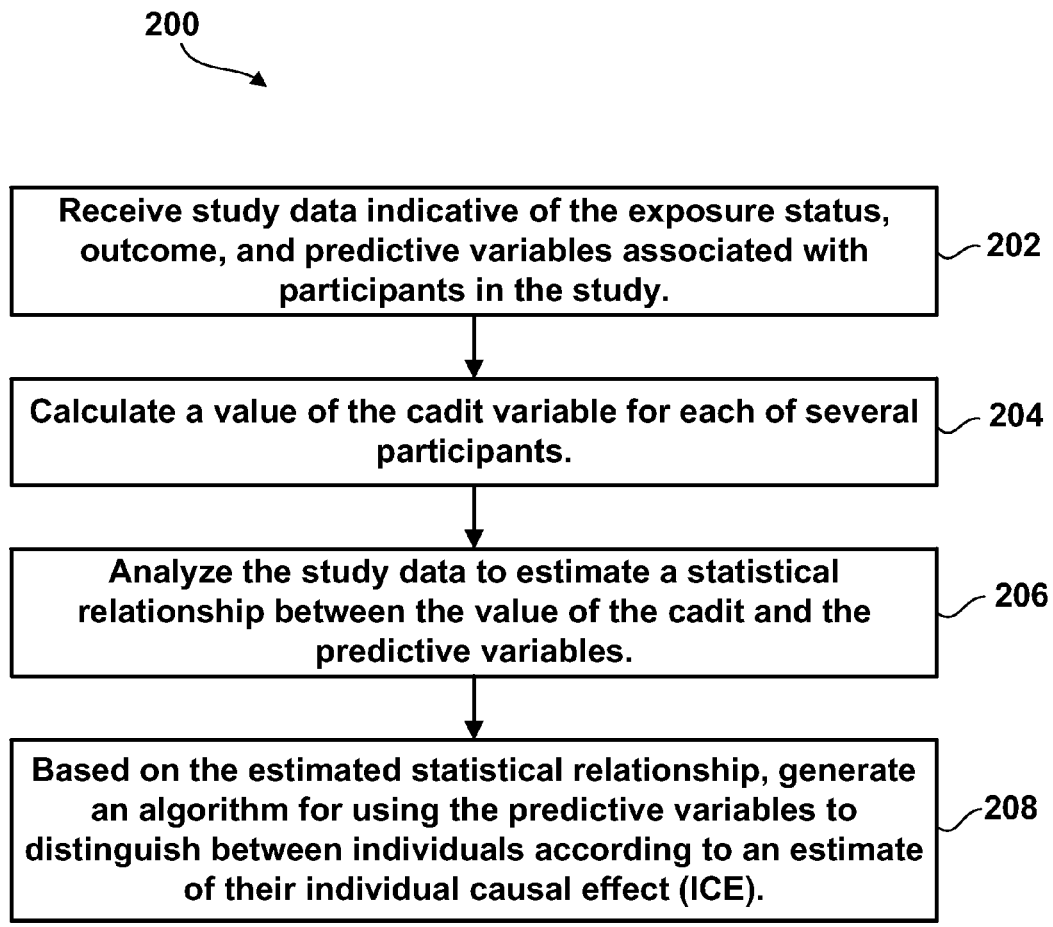
FIG. 2 is a flowchart of a process according to an exemplary embodiment.

FIG. 2 is a flowchart illustrating a method 200 according to an exemplary embodiment. Method 200 may include additional, fewer, or different operations or steps than those shown, depending on the particular embodiment. As shown, method 200 involves receiving study data indicative of the exposure status, outcome, and predictor variables associated with participants in the study (step 202). Method 200 further involves calculating a respective value of a causality variable (such as the cadit) for each of several respective participants (step 204). Also, method 200 involves analyzing the study data to estimate a statistical relationship between the value of the causality variable and the predictor variables (step 206). Further, method 200 involves generating, based on the estimated statistical relationship, an algorithm for using values of the one or more predictor variables to distinguish between individuals according to an estimate of their ICE (step 208).

Figure 3:
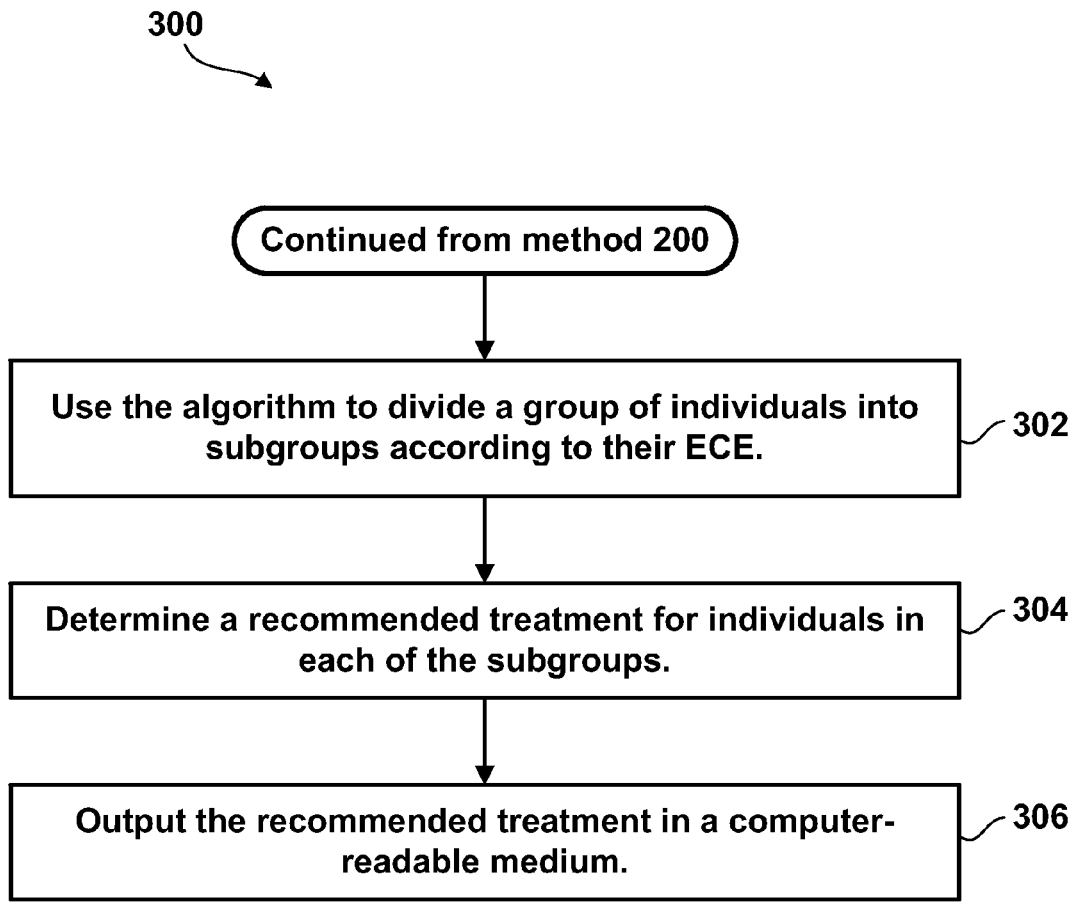
FIG. 3 is a flowchart showing process steps according to an exemplary embodiment.

FIG. 3 is a flowchart illustrating steps of an additional method 300, which may be performed along with method 200. As shown, method 300 involves using the algorithm to divide a group of individuals into subgroups according to estimates of their ICE (step 302). Method 300 also involves determining a recommended treatment for individuals in each of the subgroups (step 304). Further, method 300 involves outputting the recommended treatment in a computer-readable medium (step 306).

Figure 4:
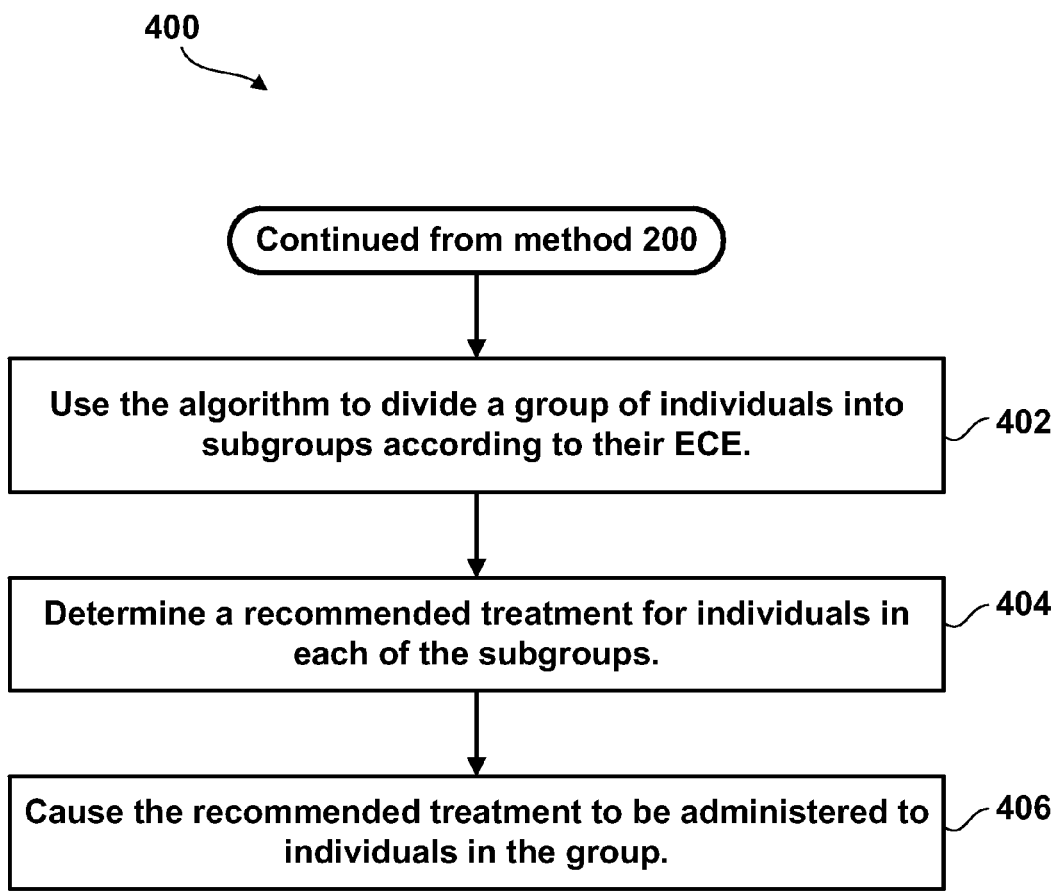
FIG. 4 is a flowchart showing process steps according to an exemplary embodiment.

FIG. 4 is a flowchart illustrating an alternative method 400 that may be performed along with method 200. As shown, method 400 involves using the algorithm to divide a group of individuals into subgroups according to estimates of their ICE (step 402). Method 400 can also involve determining a recommended treatment for individuals in each of the subgroups (step 404). Further, method 400 can also involve causing the recommended treatment to be administered to individuals in the group (step 406).

Figure 5A:
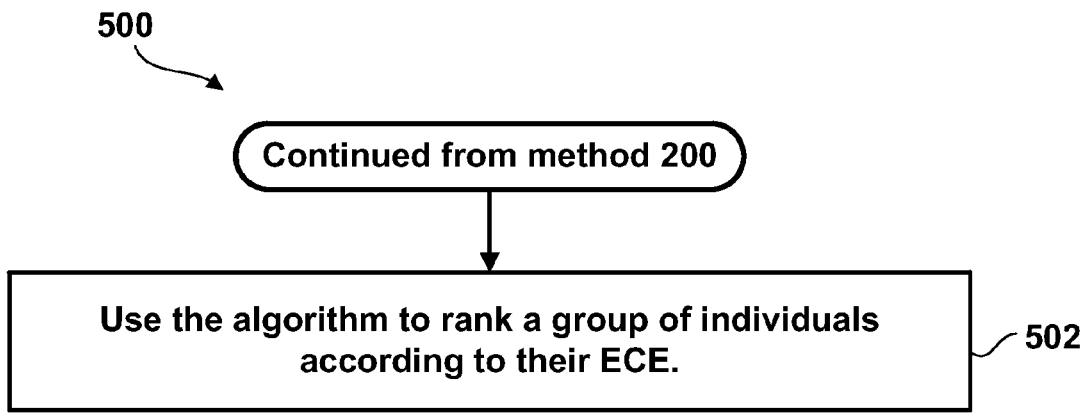
FIG. 5A is a flowchart showing process steps according to an exemplary embodiment.
Figure 5B:
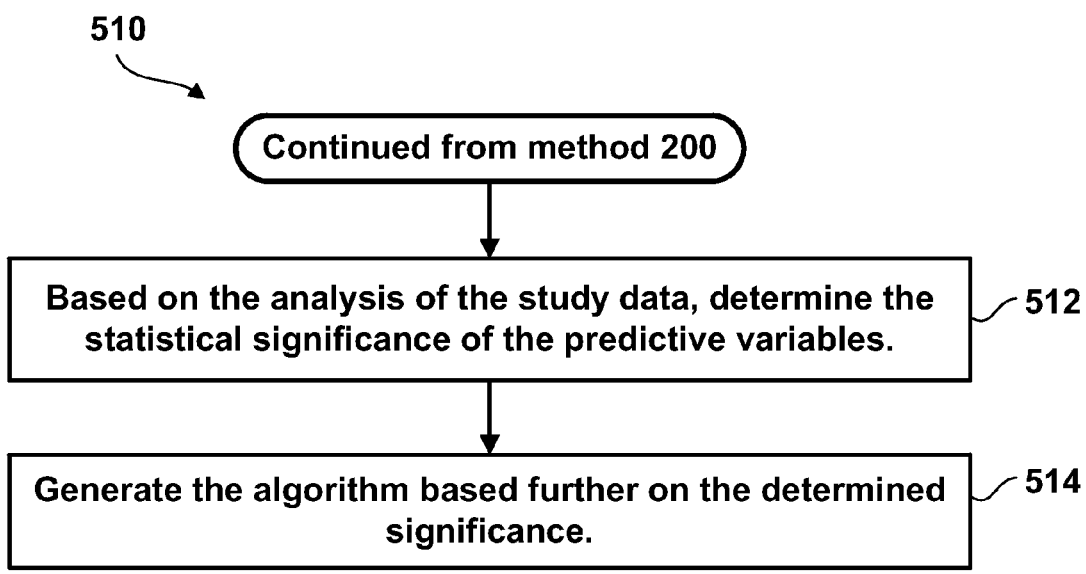
FIG. 5B is a flowchart showing process steps according to an exemplary embodiment.
Figure 5C:
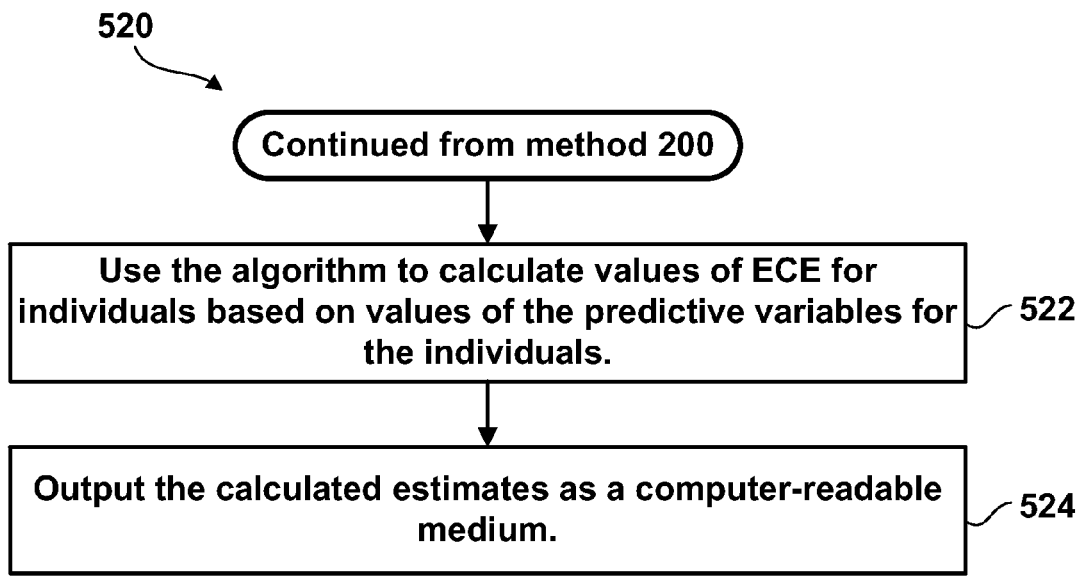
FIG. 5C is a flowchart showing process steps according to an exemplary embodiment.
Figure 5D:
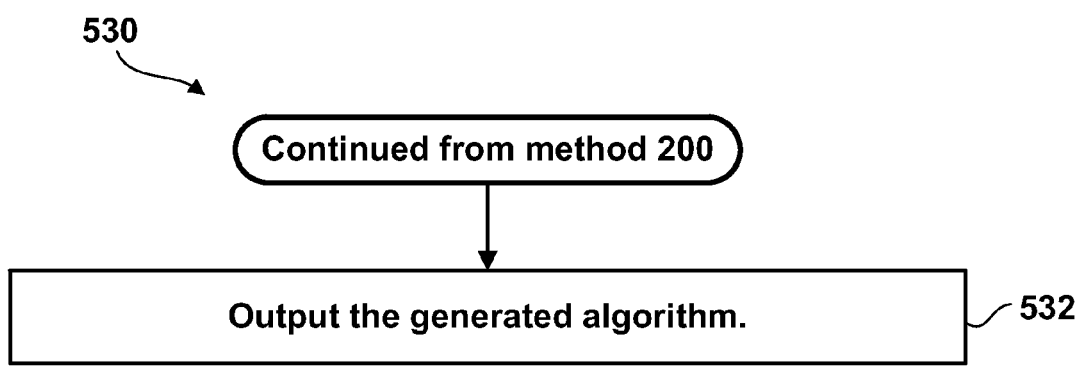
FIG. 5D is a flowchart showing process steps according to an exemplary embodiment.

FIGS. 5A-5D show several other methods that may be performed with the steps of method 200. FIG. 5A shows method 500, which involves using the algorithm to rank a group of individuals according to estimates of their ICE (step 502). FIG. 5B shows method 510, which involves, (i) based on the analysis of the study data, determining the statistical significance of the predictor variables (step 512) and (ii) generating the algorithm based further on the determined significance (step 514). FIG. 5C shows method 520, which involves, (i) based on the analysis of the study data, determining the statistical significance of the predictor variables using the algorithm to calculate estimates of ICE for individuals from values of the predictor variables for the individuals (step 522) and (ii) outputting the calculated estimates as a computer-readable medium (step 524). FIG. 5D shows method 530, involving outputting the generated algorithm (step 532).

Figure 6:
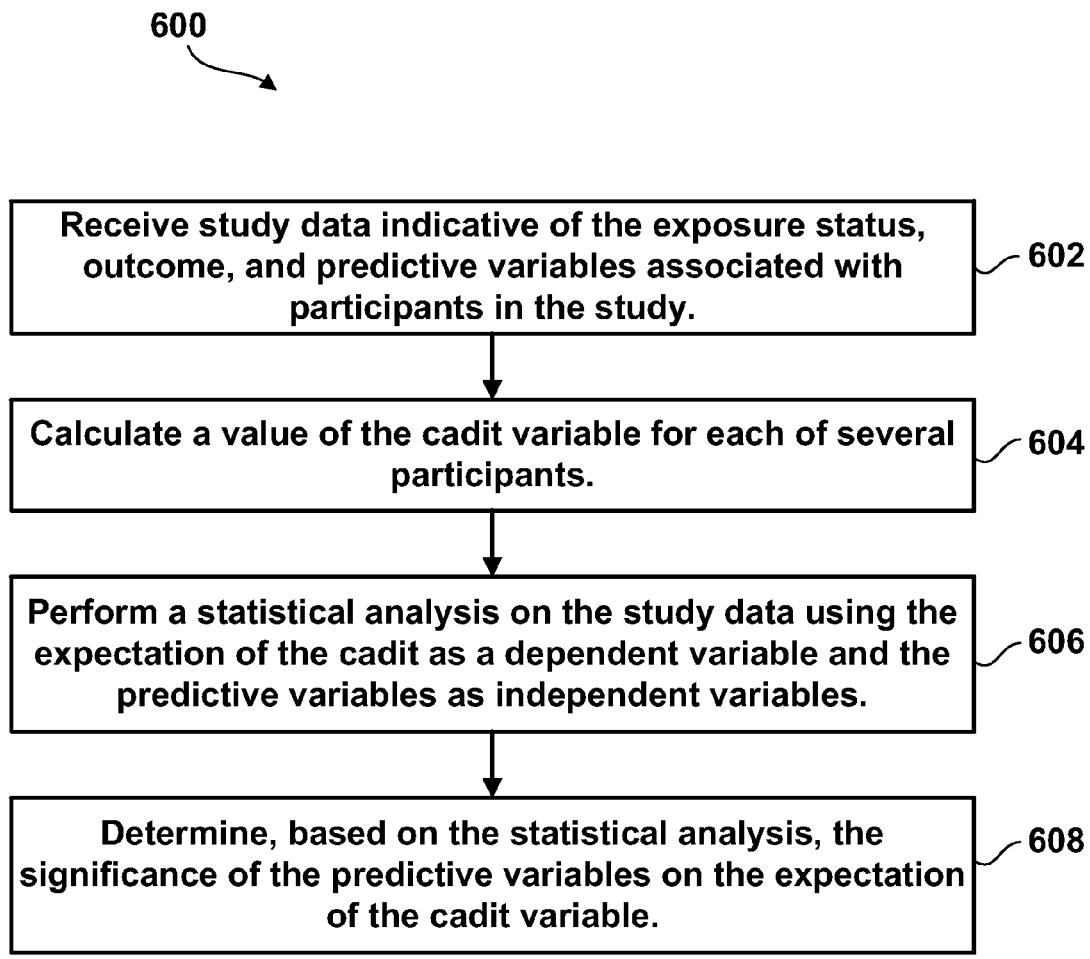
FIG. 6 is a flowchart of a process according to an exemplary embodiment.

FIG. 6 shows a method 600 for testing the significance of one or more predictor variables on an estimation of the ICE. Like method 200, method 600 and other methods depicted herein may include additional, fewer, or different operations or steps than those shown, depending on the particular embodiment. As shown, method 600 involves receiving study data indicative of the exposure status, outcome, and predictor variables associated with participants in the study (step 602). Method 600 also involves calculating a value of the causality variable for each of several participants (step 604). Additionally, method 600 involves performing a statistical analysis on the study data using the causality variable as a dependent variable and the predictor variables as independent variables (step 606). Further, method 600 involves determining, based on the statistical analysis, the statistical significance of the predictor variables on the expectation of the causality variable.

Although FIGS. 2-6 show particular example arrangements or steps, these arrangements are only examples. Method steps may be ordered in other ways and individual steps may be combined with other steps or omitted without departing from the intended examples. Example methods may also include additional techniques and steps not shown in FIGS. 2-6.

A. Receiving Study Data

A computing device or system, such as system 100, may receive study data from a variety of sources and study data may include various types of information. In some cases, study data may be received from a single source all at once. In other cases, study data may be received from several sources and/or over several receiving steps.

Study data may include data taken from one or more comparative studies. In a comparative study, participants receive any of several treatments and, then, outcome data is generated based on the responses experienced by the participants. For example, in a study of a new pharmaceutical drug, researchers may administer the drug to a first set of study participants and administer a placebo to a second set of participants. Then, the researchers may monitor any resulting health changes in the two sets and compare the responses of each group in order to gauge the benefits or risks of the drug. As another example, an advertising agency may send out a different advertisement to each of several potential customers and judge the effectiveness of the ads by how many people respond to each ad. In this second example, the "participants" may not know that they are participating in the study. Other examples may be used. As described above in the definitions, a participant need not be a person for the causal effect to be estimated using the embodiments described herein.

An ideal comparative study would involve random assignment of the exposure status to the study participants. In some studies, randomization may be useful to justify the inference that an observed difference between the groups is indicative of a causal effect. However, randomization is not necessarily required to apply the methods described here. In some embodiments, a comparative study may include historical data that was taken outside of a designated experiment or study. For example, in a study on health benefits of a particular behavior, researchers may compare health information of people who practice the behavior already to health information of people who do not practice the behavior. In some cases, the study data may be entirely made up of historical data, in other cases, the study data may be part historical and part data from a new study. In any case, the "participants" in the study may be any people whose information is used. When randomized assignment of treatment modalities is not used, some sort of statistical adjustment may be utilized to control for possible confounding bias.

A system may receive study data from various sources. For example, system 100 may receive data via communication interfaces 108. As discussed above, communication interfaces 108 may include connections to internal, external, or remote sources. Sources may be any type of computing device, server, data storage mechanism, user-input system, sensor, or combination of source types.

Study data may include observed values of exposure status and outcome, along with participant information or characteristics. The observed values may each be associated with a particular participant for which the system receives the participant information. In some cases, the study data may identify participants with one or more identifiers (e.g., name or ID number) so that the system may relate each participant's observed values and characteristics. In other cases, the study data may identify that each set of data comes from a single participant without identifying the particular participants.

Exposure status data may indicate the treatment(s) administered to each participant. In some cases, the study data may be indicative of the treatments that were administered without explicitly indicating the administered treatment. For example, in the case of a test treatment and a control treatment, the exposure status data may indicate whether each participant received the test treatment, without explicitly indicating that a control treatment was given to those who did not receive the test treatment. As another example, the study data may indicate some level of treatment (e.g., amount of treatment administered, duration of treatment, regularity of treatments etc.) administered to each participant. Then, the system may separate the level data into the various treatments, for instance, by assigning a treatment identifier to each treatment level or range of treatment levels.

Outcome data may indicate any of a variety of types of information about the participant after the treatment is administered. The outcome may represent the final condition of the participant or a condition at some set time or occasion. The nature of the comparative study may dictate what type of outcome data is relevant. For example, a study of canine medications may use each dog's health after a set time as outcome information. As another example, a study of the efficacy of political campaign ads may use each participant's voting behavior as outcome data. These examples are illustrative, but persons of skill in the art will recognize numerous types of relevant outcome data.

In some cases, several types of outcome data may be relevant. For example, in a study of potential cures for a certain disease, the final condition of the participant (e.g., cured or uncured) and the time-sensitive condition of the participant (e.g., time from treatment to recovery) may both be relevant to the study. As another example, in a study of advertisement efficacy, analysts may be interested in both (i) whether the participant made a purchase and (ii) how much the participant spent on purchases. In such cases, a system may perform separate analysis procedures to generate an ECE for each relevant outcome. Alternatively, the multiple outcome variables may be combined in some fashion to create a derived variable that represents an overall response measure.

In some cases, the outcome data may be determined at some set time after treatment is administered. In such an embodiment, the set time may be immediately after treatment, many years after treatment, or any other time that is relevant to the study. In other cases, the outcome data may be determined at the time of some event (e.g., recovery from disease, Election Day, purchase of an item, or exam time, among other examples). In still other cases, outcome may be determined at several times after treatment. For example, in a study of weight-loss programs, the outcome may be weight loss after each of several periods or whether (and how quickly) weight is regained.

In future examples, reference will be made to two major types of outcome data: Boolean and numerical. Though these example outcome types are beneficial for illustration, many other types of outcome data may be analyzed using the embodiments disclosed herein.

In a study with Boolean outcomes, each participant may have one of two possible outcome values. These two outcomes may have any values, but will usually have the conventional binary values zero and one. In what follows, any study with a Boolean outcome will be called a binary study. In a binary study, an outcome value of zero will be said to be a lack of response; an outcome value of one will be said to be a response. For example, in a study of curative medicine, the outcome may be either that the participant is cured (response) or the participant is not cured (no response). As another example, the possible outcomes of an advertising study may be that the participant made a purchase or did not make a purchase. In some cases, a system may convert numerical outcome data into Boolean outcome data for analysis. For example, a system may receive blood pressure (BP) readings in the study data and identify a certain range of readings as "healthy BP" and the remaining readings as "unhealthy BP." Other examples are possible. In a binary study, the overall value of the causal effect in the population can be represented as $\Delta = P_A - P_B$. Here $P_A$ represents the probability of a response if the participant received Treatment A and $P_B$ represents the probability of a response if the participant received Treatment B.

In a study with numerical outcomes, each participant may have an outcome that numerically quantifies the participant's condition. A numerical outcome may be represented as an integer, fraction, decimal, or other numerical expression and may be conceived as a discrete or continuous value. In what follows, a study in which the outcome has more than two possible numerical values will be called a continuous study, although the outcome may not be continuous in a rigorous mathematical sense. As one example, in a study of advertising, the numerical outcome may be the amount of money (in dollars) that a person spends or a numerical rating that the participant assigns to the ad. As another example, the outcomes of a medical treatment may be the time (in days) that the treatment takes to alleviate a health condition or symptom.

In a continuous study, we represent the outcome for participants receiving Treatment A as a random variable $Y_A$ and the outcome for participants receiving Treatment B as a random variable $Y_B$. Then the overall causal effect in the population can be represented as $\Delta = E(Y_A - Y_B) = E(Y_A) - E(Y_B)$.

In addition to exposure status and outcome, the study data may also be indicative of the values of one or more predictor variables for the participants. The predictor variables may represent any characteristic or condition of the participants as ascertained prior to treatment exposure in the study. For example, predictor variables may be demographic information (e.g., gender, age, race, ethnicity, place of residence, place of birth, family background, level of education, etc.), current personal characteristics (e.g., height, weight, blood pressure, credit score, occupation, genetic data, biomarkers, etc.), or personal history (e.g., purchase history, medical history, voting profile, behavioral history, internet browsing data, etc.) Many other characteristics and information about participants may also be included in study data. Predictor variables (also called covariates, explanatory variables, or predictors) are potentially predictive of an individual's response to a given treatment. However, the embodiments disclosed herein are not limited to situations where all, or even most, of the predictor variables are actually predictive. Indeed, the disclosed embodiments may be used regardless of how many predictor variables turn out to be predictive in the study.

Predictor variables may be categorical, numerical, or any other variable type. An example of a categorical variable is occupation, since categories like "Florist" and "Senator" do not easily translate to a numerical representation. An example of a numerical variable, on the other hand, is household income. Other variable types may also be used. Some study data may include both categorical and numerical predictor variables.

In any study, all or part of the data may be missing for some individuals. For example, some persons may elect to withhold personal information. Therefore, certain predictor variables may be omitted from some or all statistical analyses for such individuals. Alternatively, the variables may be included, but with statistical adjustment methods applied for dealing with missing data.

In some instances, a system may ignore or eliminate some of the received data. For example, if an individual's values of one or more variables are missing, it may be appropriate to exclude that individual from statistical analyses. In particular, a participant may receive a treatment but fail to report the outcome of the treatment. As another example, the system may ignore some study data in response to determining that the study groups associated with various treatment modalities are unequal in size. In this case, ignoring some data may produce more equal group sizes.

As will be shown, equalizing the group sizes may greatly simplify or facilitate analysis in some cases. In particular, in a binary study of two treatment modalities (such as an active treatment and a control), it may be advantageous to have the same number of participants receiving each of the treatment modalities. Therefore, an example process may involve determining whether the study groups are of equal size, and, if not equalizing the size of the groups. For instance, groups may be equalized by omitting the data for some participants from the larger group. Alternatively, it may be possible to effectively equalize the study groups by weighting the data or by some other type of statistical adjustment. In addition to equalizing (or effectively equalizing) the size of the treatment groups from the whole set of participants, some studies may equalize the size of treatment groups for smaller subsets of the sample pool. For example, a system may divide the participants into subgroups according to values of the predictor variables and equalize the study group sizes within each subgroup. As one particular example, if a participant's age is thought to be significant in predicting the efficacy of a treatment, then the study group may be divided according to age and the treatment-group size may be equalized for each age group so that each age group may be analyzed as if it were a separate study. As another example, in a comparative study without randomization (observational study), two or more strata may be defined such that confounding bias is believed to be absent within each of the strata. For example, each stratum may be defined in terms of a range of values for a propensity score. In effect, each such range would be treated as a separate study, within which the study groups are then equalized.

In some cases, a system may receive pre-processed study data, ready for analysis. In other cases, a system may receive unorganized or raw study data that must be processed, organized, and/or filtered before the data can be analyzed. For example, a system that receives two sets of study data that are formatted differently may need to reformat the sets of data in order to use the sets in a single analysis. As another example, a system may receive information about exposure status and predictor variables in one set of data and outcome data in a separate set of data. As still another example, a system may create derived variables suitable for analysis by transforming raw data into a different form (e.g., participant reports of wellness or side-effects after taking a study medication are converted to a numerical rating of "healthiness" or a Boolean healthy/unhealthy rating). Other examples are also possible.

B. Calculating the Causality Variable

As shown in steps 204 and 604 of FIGS. 2 and 6, respectively, the illustrated methods involve calculating a respective value of the causality variable for several participants in the study. In the following description, a particular type of causality variable, the cadit, will be used in the description. As will be described, the value of the cadit variable for a participant may be a function of the exposure status and outcome values for the participant. Additionally, as will be shown, the expectation of the cadit variable for a participant is monotonically related to the ICE for the participant. In the following section, estimating the causal effect is described with respect to currently existing indirect approaches. Then, the direct approach using the cadit variable is described.

1. Indirect Approach

To begin, suppose researchers have collected data from a randomized study comparing Treatment A and Treatment B, with the data including a set of variables (covariates) that may help predict whether or not a "response" occurs. Then, two separate statistical models are estimated from the data; one of these is based on the data for individuals exposed to Treatment A and one based on data for individuals exposed to Treatment B. For any individual, either in the original study or in some other sample, two "scores" can be generated based on these models. We will call these Score A and Score B. For a binary study, the score may be the individual's estimated probability of exhibiting a response. For a continuous study, the score may be the individual's expected value of the outcome variable.

For a binary study, Score A would represent the individual's estimated probability of exhibiting a response under Treatment A, and Score B would represent the individual's estimated probability of a response under Treatment B. Let: $X=X_1, X_2, X_3 \ldots$ represent the set of predictor variables. Let $P_{AX}$ be the individual's response probability under Treatment A and $P_{BX}$ be the individual's response probability under Treatment B. Then, we can represent Score A as an estimate of $P_{AX}$ and Score B as an estimate of $P_{BX}$. The difference between the two scores is the estimated causal effect (ECE) of receiving A rather than B for this individual.

$$\text{ECE} = \text{Score } A - \text{Score } B$$

For a continuous study, Score A would be an estimate of $E(Y_A|X)$ and Score B would be an estimate of $E(Y_B|X)$. Then the ECE would be calculated as the difference between these two estimates, i.e. $\text{ECE} = E(Y_A|X) - E(Y_B|X)$.

The most common way to derive a Score is by applying some version of regression modeling. For a binary study, the conventional type of regression analysis is called logistic regression. As will be discussed, in logistic regression modeling, the value of a set of predictor variables: $X=X_1, X_2, X_3 \ldots$ are input into a model that relates the predictor variables to an outcome variable called the logit that is a monotone function of a probability. Such a model can be fitted separately to the data from the group that receives Treatment A and the data from the group receiving Treatment B. In this way, the probability of a response under Treatment A ($P_{AX}$) and the probability of success under Treatment B ($P_{BX}$) can be estimated as functions of the predictors.

A similar two-model approach can be employed in a continuous study. In that case, ordinary least-squares (OLS) regression is usually applied to estimate $E(Y_A|X)$ based on the data from the study group receiving Treatment A, and $E(Y_B|X)$ based on the data from the study group receiving Treatment B. Then, the difference between these two estimates provides the ECE for an individual based on their values of the predictor variables X.

In general, the ECE for each individual is calculated by taking the difference between the two values, Score A and Score B, generated by a regression model or another technique. A variation on the two-model approach to estimating the ICE is to derive a single model that incorporates so-called interaction effects. Such an interactive model accomplishes essentially the same objective as the two-model approach. Although it can be implemented as a single model, this interactive model implicitly incorporates two separate models: one that predicts the outcome if an individual is exposed to Treatment A and another that predicts the outcome if the individual is exposed to Treatment B.

Whether a two-model or interactive model approach is utilized, there is a serious drawback related to what statisticians call the problem of model specification. Model specification refers to the mathematical form of the model. In general, a dependent variable is assumed to be a particular mathematical function of various independent variables. Model specification involves two aspects: selecting the mathematical form of the model and determining which particular independent variables to include in the model. The critical problem of model specification is complex and challenging, especially when there are many potential predictors from which to choose. In the context of developing a statistical model to predict an ICE, the dependent variable is the outcome and the independent variables include the exposure status and one or more predictor variables.

In applying the conventional indirect approach, model specification is particularly problematic. This approach attempts to optimize the two models separately, and then estimate the ICE as a difference between the estimated outcome value generated by each of the models. For example, a particular variable might strongly increase the probability of a positive response, regardless of the treatment. This variable, therefore, might receive a large coefficient (weight) in each of the two models (or the interactive model), because it improves the prediction of $P_{AX}$ and $P_{BX}$ separately. However, since this variable may have little impact on the ICE (it increases predicted values of both $P_{AX}$ and $P_{BX}$) such a variable may have little impact on (or even worsen) the prediction of the ICE.

2. Direct Approach

An insight of the present inventors is that in order to facilitate direct estimation of the ICE, study data may be transformed to create a special dependent variable that is a measure of the causal relationship between the exposure status and the outcome. In particular, the expectation of this dependent variable, named herein the cadit variable, is monotonically related to the ICE. This relationship may be beneficial in overcoming the fundamental problem of being unable to observe the outcome for the same individual under alternative treatment modalities. In a binary study, the cadit may be a high value if the exposure status and outcome value are concordant, in a sense defined below. And the cadit may be a low value if the exposure status and outcome value are discordant. In a continuous study, the value of the cadit variable may be an increasing monotone function of the value of the outcome for participants who receive a first treatment modality and a decreasing monotone function of the value of the outcome for participants who receive a second treatment modality.

To motivate the definition of the cadit variable, first consider a binary study with two possible values of exposure status (i.e., a study in which each participant is exposed to one of two treatment modalities and the outcome is either that a response event occurs or that the response event does not occur). The four possible combinations of treatment modality and outcome value are shown below. The letter shown in each of the cells represents the number of participants who satisfy the conditions of that cell:

|  | Event | No Event |
| --- | --- | --- |
| Treatment A | a | b |
| Treatment B | c | d |

In this example, the more strongly there exists a causal effect such that Treatment A is more likely to elicit the response event than Treatment B, then the higher will be a participant's probability of falling into one of the "concordant" cells: "a" and "d"; rather than into one of the "discordant" cells: "b" and "c". Therefore, the proportion of participants in cells "a" and "d" is an indicator of the strength of the causal effect. For example, if there is no causal effect of Treatment A relative to Treatment B, then roughly as many participants will be in the concordant cells as in the discordant cells.

Therefore, in a binary study, the cadit may be defined as: cadit=1, for participants in cell "a" or cell "d" and cadit=0, for participants in cell "b" or cell "c". Therefore, the value of the cadit variable for each participant in a binary study may be either one or zero depending on the exposure status and outcome for that individual. In a mathematical representation, the cadit variable may be defined as: cadit=T×R+(1−T)×(1−R), where T is the exposure status (T=1 for Treatment A and T=0 for Treatment B) and R is the outcome (R=1 if a response event occurred and R=0 if the response event did not occur). Although the numerical examples of one and zero are used in this implementation, other values may be used in other example implementations.

The cadit variable in a continuous study may be defined in a similar manner as the cadit in the binary case. For each individual, i, let $Y_i$ be the observed value of the outcome for the individual and $\bar{Y}$ be the mean of all the observed values (i.e., the average value for both study groups combined) of the outcome. Then, the following equations define the value of the cadit variable (Z) for a participant in the continuous study (in which t is the proportion of participants that received Treatment A).

$$Z_i = \frac{Y_i - \bar{Y}}{2t(1-t)} \text{ if } T = 1 \text{ for subject } i$$

$$Z_i = \frac{-(Y_i - \bar{Y})}{2t(1-t)} \text{ if } T = 0 \text{ for subject } i$$

As evident from the above definition for the cadit with a binary outcome Variable, R, the cadit variable will be positive to the extent that the outcome and exposure status are "concordant" in the sense that $Y_i$ is above average for individuals who receive Treatment A and/or below average for individuals who receive Treatment B). Conversely, the cadit variable will be negative to the extent that the outcome and exposure status are "discordant" in the sense that 1 is below average for individuals who receive Treatment A or above average for individuals who receive Treatment B. The participants associated with positive cadit values, therefore, roughly correspond to the participants that occupy cells "a" and "d" in a binary study. Likewise, the participants associated with negative cadit values roughly correspond to the participants that occupy cells "b" and "c" in a binary study.

It can be shown that in a continuous study the expected value of the cadit Z is equal to the ICE. Note that when the study has t=0.5, then the formulas for $Z_i$ simplify. Also, it can be shown that in this case the main properties of the cadit for a continuous study would still hold even if $\bar{Y}$ were replaced by any constant. However, using $\bar{Y}$ has some desirable statistical properties.

Though example values of the cadit variable for binary and continuous studies are defined herein, other cadit variable values may be defined for other types of experiments. For example, in a binary study with more than two treatment modalities, the value of a cadit variable may be defined for estimating the causal effect of receiving one treatment modality rather than any of the other treatment modalities using similar techniques as those used to define the cadit for the binary study with only two modalities.

A computing device or system may calculate a respective value of the cadit variable for each participant upon receiving the study data. If values of exposure status and/or outcome are missing for a participant the system may refrain from calculating the value of a cadit variable for that participant. In some cases, the system may automatically determine the cadit variable to use and calculate the values of the cadit variable without requiring user-input. In other cases, the system may prompt for user-input to define the cadit variable(s) to be used in analysis.

C. Analyzing the Study Data

As shown at steps 206 and 606 of FIGS. 2 and 6, respectively, the system may use the calculated values of the causality variable to analyze the study data. Such analysis may help the system to determine a statistical relationship between the causality variable and the values of the predictor variables. In this description, a statistical relationship is typically a mathematical relationship in which the expectation of a dependent variable is a mathematical function of the values of the independent variables. Such a mathematical relationship may be an algebraic relationship in which one variable is an algebraic function of another variable. As with calculating the causality variable, the following section will focus on the particular examples of the binary study and the continuous study.

In a binary study, each observation may be regarded as a random variable that can occur as either a low value (for no response) or a high value (response). The expectation of a random variable (also called the expected value, mean value, or first moment) is the average value of the variable. For a binary study where the high value is 1 and the low value is 0, the expectation of the cadit variable is simply the probability that the cadit is 1 for a participant in the study. This cadit probability (herein termed $P_c$) may be estimated as the ratio of participants for which the cadit variable is a high value (e.g., 1) to the total number of participants for which the cadit has been calculated. As a particular example, in a study in which Treatment A has a perfect causal effect relative to Treatment B (i.e., each person given Treatment A has a response, and no person given Treatment B has a response), the expectation of the cadit variable may be 1.0. Alternatively, in a study in which Treatment B has a perfect causal effect relative to Treatment A, the expectation of the cadit may be zero. Further, in a study in which there is little to no causal effect of either treatment modality relative to the other, the expectation of the cadit may be somewhere near 0.5.

To estimate the causal effect for an individual with a set X of predictors, we can estimate a conditional effect (ICE): $\Delta_X = P_{AX} - P_{BX}$. Then, it can be shown that the following mathematical relationship holds: (t is again the proportion of participants that are given Treatment A):

$$\Delta x = 2P_{cX} - 1 - (2t-1)(P_{AX} + P_{BX} - 1)$$

In many studies, the same number of participants may receive each treatment, making the value of t, t 0.5. In this special case, the conditional causal effect is simply:

$$\Delta_X = 2P_{cX} - 1$$

This simplification is a motivation for the normalization of the treatment group sizes discussed in section III (B) above. In this special case where t=0.5, when there is no causal effect ($\Delta_X=0$), then $P_{cX}$, the expectation of the cadit variable, is 0.5. Also, when there is perfect causality for Treatment A vs. Treatment B ($\Delta_X=1$), the expectation is 1.0.

It should be noted that alternative high and low values of the cadit variable may be chosen without departing from the structure of the cadit. If high and/or low values of the cadit are defined in a different manner, then the formulas for the group causal effect may also change. For example, if the low value of the cadit variable is −1 instead of 0 {cadit=TR+(1−T)(1−R)−T(1−R)−R(1−T)}, then the relation between the group causal effect and the expectation of the cadit variable would be:

$$E(cadit|X) = \Delta_X + 2(t-0.5)(P_{AX} + P_{BX} - 1),$$

which simplifies to $E(cadit|X) = \Delta_X$ when $t=0.5$.

In a continuous study, an expectation of the cadit variable may be calculated from the values of the cadit variable for individuals in the study. This is possible because of the following relationship between the ICE and the cadit variable Z:

$$E(Z|X) = E(Y_{AX} - Y_{BX}|X) = \Delta_X$$

So, by estimating the conditional expectation of Z, a direct method of estimating the value of $\Delta_X$ may be obtained.

In particular, for values of X when there is no causal effect ($\Delta_X=0$), the expectation of the cadit variable will be zero. Similarly, when Treatment A has a positive causal effect relative to Treatment B ($\Delta_X > 0$), the expectation of the cadit will also be positive.

In any type of comparative study, a statistical relationship between the causality variable and the values of the predictor variables may be estimated through statistical analysis. As defined above, X is a set of predictor variables ($X_1$, $X_2$, $X_3$ . . . ) for which values are obtainable for an individual or group of individuals. A system may determine the causal effect for individuals having a given set of values for the set of variables X by fitting the study data to a model. The fitting process may use any technique for model estimation with the causality variable as the dependent variable and the variables X as the independent variables. For example, in a binary study, the process may involve logistic regression. In a continuous study, the fitting process may involve linear regression (e.g., polynomial regression, OLS regression, Bayesian linear regression, etc.) Model fitting may also involve other fitting algorithms, such as decision-tree analysis or classification and regression tree (CART) analysis, to fit the data to a particular model.

In the example of logistic regression, the general form of the model may be:

$$\ln\left(\frac{P_{cX}}{1 - P_{cX}}\right) = g(X) = \alpha + \beta_1 X_2 + \beta_3 X_3 + \ldots + \beta_k X_k$$

In this model, $P_{cX}$ is the conditional expectation of the Boolean cadit variable for the set of variables defined by X and $\alpha$, $\beta_1$, $\beta_2$, $\beta_3$, etc. are constant model coefficients. These coefficients can be estimated by standard algorithms and implemented using commonly available statistical software. The resulting model represents a mathematical relationship between the value of predictor variables ($X_1, X_2, X_3 \ldots$) and the conditional expectation ($P_{cX}$) of the cadit variable.

In the example of linear regression, the general form of the model may be:

$$E(Z|X) = h(X) = \alpha + \beta_1 X_1 + \beta_2 X_2 + \beta_3 X_3 + \ldots + \beta_k X_k$$

In this model, $E(Z|X)$ is the conditional expectation of the continuous cadit variable, Z, given the values of the predictor variables X. The model parameters ($\alpha$, $\beta_1$, $\beta_2 \beta_3$, . . . $\beta_k$) in this model may be determined through a variety of methods such as OLS, weighted least squares, or least absolute shrinkage and selection operator (LASSO) analysis. It will be clear to those of skill in the art that the analysis can be performed in other ways to produce the estimated mathematical relationship between the conditional expectation of the causality variable and the values of the predictor variables.

D. Testing the Statistical Significance of the Predictor Variables

As shown in step 512 of method 510 and step 608 of method 600, an example embodiment may include the step of testing the statistical significance of the variables on the causal effect. More specifically, the full set of regression coefficients in the model $\alpha_1$, $\beta_2$, $\beta_3$, etc., or any subset of these coefficients could be tested. There are several ways to perform such a test, including via a classical frequentist hypothesis test or confidence interval approach, or through a Bayesian method, such as a credible interval based on a posterior distribution. The basic idea is to determine whether there is statistical evidence that the estimated coefficients truly differ from zero, or from some other specified null-hypothesis value.

In classical statistics, the statistical significance for any parameter is a measure of the extent to which the estimated value of the parameter is consistent with random chance. The usual measure of statistical significance is the p-value, which is the probability that if the parameter were truly zero (or some other specified "null" value), a result at least as extreme as the one actually observed would occur. By extreme is meant deviating from the null hypothesis value. Generally, the smaller the p-value, the less likely that random chance provides a plausible explanation. In the present embodiments, the statistical significance of each predictor variable, or any set of these variables, may be tested to determine whether the variable(s) are significantly related to the causality variable. Then, because the expectation of the causality variable is a monotonic function of the ICE, this method provides a test of the significance of the statistical relationship between the predictor variable(s) and the ICE.

Statistical significance may be determined in a variety of ways. The particular testing procedure employed depends on the type of statistical model. For example, if OLS regression is used, then the traditional t-test and F-test can be utilized for this purpose. Generally, regression relates predictor (independent) variables to output (dependent) variables. In the present methods, a dependent variable of importance is the causal effect. Since the causal effect is related to the value of the cadit variable, testing may be performed using the cadit variable as the dependent variable and any set of the predictor variables as independent variables. Hence, the variables are tested for their significance on the causal effect (e.g., a difference between expected response rates or mean response values) of the treatments and not necessarily for their significance in determining the response value.

Some tests of significance may evaluate the significance of several (or all) of the predictor variables as a group to determine significance for the set of variables, Statistical significance testing may thus help to facilitate identification of variables that are more or less important to accurate estimation of the causal effect. In practice, though, relevant predictor variables may be selected also based on any number of independent validation processes, rather than on statistical significance alone. Validation testing may include cross-validation based on the study data, as well as analyzing data from additional sources (e.g., holdout samples, new samples, historical studies, etc.) to independently confirm a result. For instance, the confirmation could be based on examining the relative causal effects in a new sample for those individuals predicted to be in the top decile, next decile, etc. In this case, an indication that the model is performing well might be that the individuals with ECE values in the highest decile displayed the largest difference, among the ten deciles, between the observed rates of response for alternative treatment modalities.

In some embodiments, variables that are found to be irrelevant may be ignored in analyzing the data, fitting the data to a model, generating an algorithm for distinguishing between individuals, and/or using the algorithm. For example, in response to determining that only one variable is relevant to predicting the causal effect of the treatments in a certain study, a system may remove all the other variables from a model to improve the model's performance. Such a procedure may be performed at step 514 of method 510.

E. Generating an Algorithm for Distinguishing Between Individuals in Accordance with their ECE As shown in step 208 of method 200, an example process may involve generating an algorithm, based on the estimated statistical relationship, for using the predictor variables to distinguish between individuals according to their estimated causal effect (ECE). The algorithm may be for generating the ECE so that individuals may be distinguished by the ECE. In other cases, the algorithm may score or rank the individuals without needing to calculate an actual ECE.

One example of an algorithm is a mathematical formula relating the predictor variables to the causal effect. For example, a system may simply use the determined mathematical relationship between the expectation of the cadit and the predictor variables as an algorithm for generating the ECE. In such an embodiment, the system may modify the formula so that the output is a causal effect ($\Delta_X$), rather than the expectation of the cadit variable ($P_{cX}$ or $E(Z|X)$). For example, in a binary study with equal-sized study groups, the formula $\Delta_X = 2P_{cX} - 1$ could be used to perform such a modification.

In another embodiment, the system may use the expectation of the causality variable as a score for distinguishing individuals. Since the expectation of the cadit is monotonically related (and in some cases equal) to the estimated causal effect (ECE), an increase in the expectation of this type of causality variable corresponds to an increase in the value of the ECE. Therefore, a system may effectively distinguish between individuals in accordance with their ECEs by distinguishing in accordance with the expectation of the cadit variable for the individuals.

In another embodiment, the system may use some other mathematical function that is monotonically related to the ECE as a score for distinguishing individuals. For example, the functions $g(X)$ and $h(X)$ defined above respectively may be used in this manner. Since the values of these functions are monotonically related to the expectation of the respective cadit variables, an increase in these functions corresponds to an increase in the value of the causal effect. Therefore, a system may effectively distinguish between individuals in accordance with their values of $g(X)$ and $h(X)$.

If a particular embodiment fits data to a structure other than a mathematical formula, then the algorithm may use a similar structure. For example, in an embodiment that uses decision tree analysis to relate the predictor variables to the expectation of the cadit, the system may generate a tree-structured algorithm for distinguishing individuals.

In some embodiments, a system may generate an algorithm that uses only some of the predictor variables to distinguish between individuals. For example, the system may use the results of a statistical significance test to determine that several variables are not significantly related to the ICE and, in response to this determination, omit the insignificant variables from any mathematical expressions or procedure steps in a generated algorithm. As another example, validation testing on a hold-out sample may reveal that inclusion of certain potential predictor variables reduces the algorithm's predictor accuracy in practice. Other example algorithms may also be generated.

F. Using the Generated Algorithm

FIGS. 3, 4, 5A, 5C, and 5D show example steps that may be performed to use a generated algorithm or generated ECE. In addition to the illustrated steps, other example procedures could also be performed in combination with method 200.

The steps of FIG. 3, in combination with method 200 of FIG. 2, show a method 300 for producing and outputting a recommended treatment for individuals in accordance with the ECE for the individuals. In particular, method 300 involves using the algorithm to divide a group of individuals into subgroups according to their ECE (step 302). Method 300 also involves determining a recommended treatment for individuals in at least one of the subgroups (step 304). Further, method 300 involves outputting the recommended treatment(s) in the form of a computer-readable medium (step 306).

As shown in step 302, a computing system may use the generated algorithm to divide individuals into groups based on their ECE. In this step and all subsequent steps, the individuals could be the participants in the original study, participants in a new study, or any individuals for whom values of the predictor variables are available. Although this method involves dividing a group into subgroups, this and the methods described below may effectively be used on single individuals. For example, a system may define characteristics for individuals in certain subgroups and, then, sort the single individual into one of the subgroups based on their characteristics.

A system may divide individuals in a variety of ways. In some embodiments, the system may generate an ECE for each individual and sort the individuals into subgroups based on their respective values of ECE. For example, if the values of ECE range from some maximum to some minimum value, then the system may set several intermediate values between the maximum and the minimum as dividers between subgroups. As another example, the system or algorithm may have preset values of ECE that define the edges of subgroups. In some cases, the subgroup definitions may change dynamically as data for new individuals is added to study data.

In other embodiments, the algorithm may define particular subgroups into which individuals may be divided. In such an embodiment, the system may simply apply the algorithm to individuals in order to divide the individuals into appropriate subgroups, without explicitly generating an ECE for each individual. As with the system-defined subgroups, the algorithm may use either predefined or changeable subgroup definitions.

At step 304, the system determines a recommended treatment for each subgroup. The recommended treatment may be a specific treatment action (including refraining from performing an action) or a recommended amount of treatment that should be performed (e.g., dosage, level of interaction, amount of discount for a special offer, etc.) As a particular example, if the study is a test of a medical cure, and a positive value of ECE indicates a curative effect on the individual, then the system may recommend administering the medical cure to the subgroup of individuals with positive values of ECE. In some cases, more than one subgroup may receive the same recommended treatment. Further, in some cases, more than one recommended treatment may be offered as potential recommended treatments. For example, a system may determine that, for a given subgroup, two treatments would have some beneficial causal effect and, responsively, the system may recommend either treatment. Other examples are also possible.

At step 306, the system outputs the recommended treatment, in some cases, system 100 may output the recommended treatment via communication interfaces 108 to integral, local, or remote computing devices or systems. For example, system 100 may output a recommended treatment to a display screen so that a user may view the treatment recommendations. As another example, a system 100 may output the recommended treatment as a data-file to a remote server for analysis. As yet another example, the recommended treatment may be output onto a local storage device or medium.

In some cases, the system may output a list of individuals in subgroups along with the recommendation for the individuals or the subgroups. For example, a database file may include a list of individual identifiers with the recommended treatment associated with each identifier. As another example, a database file may list the individuals in each subgroup and separately list the recommended treatment(s) for the subgroup. In other cases, the system may output the values of ECE for each individual along with a list the recommended treatment(s) and range of ECE values for each subgroup. In other cases, the system may output just the treatments and range of ECE values for each subgroup, without including lists of individuals in each subgroup. In still other cases, the system may filter out individuals for whom the recommended treatment requires no active interaction (e.g., do not offer discount, refrain from administering medical therapy, do not test again, etc.) and output a list of only the individuals for whom the recommended treatment requires action. In the example of a single individual, the system may simply output the recommendation and/or the ECE for the individual.

FIG. 4 also shows a method 400 that involves dividing individuals into subgroups (step 402) and determining a recommended treatment for the subgroups (step 404). Method 400 further involves causing the recommended treatment to be administered to individuals in the subgroup. In this embodiment, instead of outputting data related to the recommended treatment, the system outputs an instruction to a connected system to administer the treatment. For instance, if the treating system is controlled by a computing system, then system 100 may transmit a computer-executable instruction to the treatment control units. As a particular example, a direct advertiser may use method 400 to determine a subgroup of individuals for whom a particular email advertisement may be effective and, in response to receiving the results, automatically transmit the email advertisements to addresses associated with the individuals. As another example, a computerized music-streaming service may determine a subgroup of individuals that would positively react to a particular musical selection and automatically begin playing that selection for the individuals.

FIG. 5A shows an additional method step that may be used in combination with method 200 to produce method 500. In particular, method 500 involves using the generated algorithm to rank a group of individuals according to their ECEs. For example, the system may place each individual in order from lowest value of ECE to the highest value of ECE. In some cases, the system may omit some individuals from the rankings (e.g., individuals with negative values of ECE are omitted, individuals with values in the lowest quartile are omitted, etc.) In some embodiments, the rankings may be outputted in the form of a computer-readable medium, communication signal, or executable instruction. In some cases, rankings may include study participants. Rankings may also include individuals who were not in the original study. Further, rankings may include study participants from any comparative study, other added individuals, and/or historical data. In the example of a single new individual, the individual may be placed in the rankings of previous stored rankings.

FIG. 5C shows additional steps that can be combined with method 200 to produce method 520. Method 520 involves using the generated algorithm to calculate an ECE for individuals from values of the predictor variables for the individuals (step 522). For example, the system may determine the expectation of the cadit variable for each individual or group and, then, use the known relationship between E(cadit) and the group causal effect (A) to calculate the ECE of the treatment for the individual. In this sense, the "group" causal effect is the estimated causal effect for individuals that share all the same values of the predictor variables, as estimated from data for people who share some values of the variables. Hence, the group causal effect may be estimated even if data is not available for any full members of the group. For the binary case, the group causal effect may be determined by the formula: $\Delta = 2P_c - 1$, where $P_c$ is the expectation of the cadit. For the continuous case, the group causal effect is equal to the expectation of the cadit variable. In some cases, the system may refrain from calculating values of ECE for certain individuals (e.g., negative values of ECE may be ignored; individuals with values in the lowest quartile are ignored; etc.)

Method 520 also involves outputting the calculated values in the form of a computer readable medium. In some embodiments, the rankings may be outputted in the form of a storage medium, communication signal, or executable instruction. Calculated values may include values from study participants, individuals outside of the original study, other added individuals, and/or historical data. In the example of a single new individual, the calculated value may be simply output without any corresponding identifier. For other situations, the ECE data may be linked to a list of individuals.

FIG. 5D shows an additional method step that may be used in combination with method 200 to produce method 530. In particular, method 530 involves outputting the generated algorithm. For example, the generated algorithm may be output in the form of a computer-readable medium. Such a medium may include memory, program instructions, and displays of information. In some cases, the system may output a depiction of the algorithm, such as a flowchart, set of equations, or pseudocode. In addition to the standard algorithm, the system may output instructions for performing additional method steps such as dividing individuals into subgroups, ranking individuals, determining an ICE, outputting a recommended treatment, and/or causing a recommended treatment to be performed.

In some embodiments, certain subgroups whose members have especially high (or low) values of ECE may comprise recognizable profiles. These profiles may involve specific patterns of variables that are interpretable as certain well-known types of individuals. As such, they can provide insight into causal dynamics and perhaps lead to more refined further analyses. For example, a profile of "soccer mom" may be associated with particular values of marital status, family status, age, gender, employment history, residential area, ages of children, purchasing history, and/or political preference. As another example, if a participant is a household, a profile of "middle-class family" may be associated with particular ranges of household income and certain values of marital status, family status, and employment history for members of the household. Once a profile is established, it may be used in a variety of ways, including as an independent predictor variable.

IV. Example Application

Customer Relationship Marketing

For dealing with a relevant population, such as existing customers or new prospects, a business may use business statistical modeling, called predictive analytics or business analytics. A primary aim of predictive analytics is to match each individual in the population with the action that will be most effective in causing a desired response, such as the purchase of a certain product or retention as a customer. In this context, the action being evaluated typically takes the form of an inducement (promotion, discount, advertising, etc.) intended to evoke the response. To evaluate the efficacy of a campaign involving such an inducement, a company may run a randomized experiment. The causal effect (change in response rate) estimated in the experiment is the "lift" attributable to the inducement.

However, businesses may attempt to deploy these inducements judiciously, since an inducement typically entails some cost. In some cases, the inducement may actually be counterproductive. That is, it may "turn off" the customer or prospect and decrease the chances of success.

Predictive modeling may be performed "passively" via statistical analysis of a large sample of individuals who have previously received the inducement. For each individual, the outcome is observed and factors believed to affect the probability of a response are measured. Then, the statistical model is developed using this dataset. Based on the resulting model, individuals are scored and ranked in terms of their predicted response probabilities. Those whose score exceeds some threshold, intended to optimize a cost-benefit trade-off, are then targeted to receive the inducement.

Unfortunately, the expected lift for this targeted stratum of the population is not known, and may not actually be increased over the general lift in the population. In some cases, the actual lift in the targeted population may be determined only after the modeling is complete and a target population has been specified. When the campaign is then deployed to the target population, a randomly selected control group may also be followed. Then, the actual effect of the intervention can be determined. This post hoc type of validation is useful for evaluating whether or not the predictive model has performed well, and perhaps, whether it should be used in the future. However, this approach may be of limited value, since it does not indicate how to improve the targeting by focusing on those that are most likely to be influenced by an inducement.

In the context of database marketing, potential customers may be divided conceptually into four response types depending on, first, whether they will buy a product when presented with an inducement and, second, whether they will buy the product when not presented with an inducement. Each type is shown in the following table along with the typical descriptive terminology.

| Hypothetical Sales Promotion | | | |
|---|---|---|---|
| Will the customer buy? | | | |
| Response Pattern | Induced | Not Induced | Proportion |
| 1: Sure Thing | Yes | Yes | $P_1$ |
| 2: Persuadable | Yes | No | $P_2$ |
| 3: Sleeping Dog | No | Yes | $P_3$ |
| 4: Lost Cause | No | No | $P_4$ |

Passive modeling effectively attempts to identify characteristics of individuals who will respond (e.g., buy the product). For example, if the inducement is already being provided routinely to customers, the statistical model may identify characteristics of existing customers correlated with higher rates of buying. However, this group includes people who would buy regardless of the inducement (Sure Things) in addition to those who are influenced to buy by the inducement (Persuadables). It may be undesirable to target "Sure Things" because such advertising adds cost but generates no incremental payoff. Furthermore, such a model is unlikely to identify individuals who would react negatively to a promotion (Sleeping Dogs), because these will (if offered the inducement) be indistinguishable from the Lost Causes.

Using a method like those shown in FIGS. 2-5D, especially with the novel cadit variable, may help to solve this problem. In particular, a comparative study may be conducted in which some participants (e.g., customers) are presented with an inducement and other participants are not offered the inducement. Using the methods outlined above, individuals may be distinguished from one another based on their ECEs. In this situation, a subgroup of individuals with an ECE close to zero would include mainly Sure Things and Lost Causes. A subgroup characterized by relatively high positive values of the ECE would include many Persuadables, and a subgroup characterized by negative values of the ECE would include many Sleeping Dogs. Based on the characteristics (predictor variables) associated with customers in each identified subgroup, a set of characteristics that are correlated with high values of ECE may be identified. Then, a subset of potential customers who share these characteristics may be identified from a population who have not been included in the study. Offering the inducement to such a subset should result in a higher average true causal effect than would be achieved in the general population.

As a particular implementation, a software program may be provided to facilitate determining to which potential customers an inducement should be offered. Such a software program may receive, as an input, purchase activity data for potential customers that did or did not receive an inducement, along with demographic or other characteristic data for the customers. The software may then perform the process steps shown in FIG. 2 to generate an algorithm that uses the characteristic data to distinguish between potential customers. The software may then cause the system to send or display, as an output, the generated algorithm or the results of using the algorithm on a set of customers. The results may be a ranked or subdivided list of potential customers and may include ECE values for each customer. In other cases, the software may cause an automated advertising system to send inducements to a set of potential customers that were chosen according to their ECE values. In this way, the automated system may automatically send inducements to those recipients that are more likely to be positively influenced by the inducement.

V. Example Application

Personalized Medicine

A problem, recognized by the present inventors, that medical researchers face in the context of clinical trials is conceptually quite similar to that addressed by marketers. The table below illustrates how the situation can be represented in a biomedical context:

| Hypothetical RCT | | | |
|---|---|---|---|
| Will the patient die? | | | |
| Response Pattern | Drug | Placebo | Proportion |
| 1: Doomed | Yes | Yes | $P_1$ |
| 2: Causal | Yes | No | $P_2$ |
| 3: Preventive | No | Yes | $P_3$ |
| 4: Immune | No | No | $P_4$ |

In the medical research context, passive modeling to identify factors that influence a response is termed "prognostic" modeling. The term "predictive" modeling is reserved for modeling to identify factors that can influence the causal effects of treatments. So, in this context, cadit modeling can be regarded as an improved methodology for predictive modeling.

While the structure is similar to that of business analytics, such as analysis of a sales promotion, the demands of modeling in the medical environment are different. Unlike the business context, the medical research environment is highly regulated. In business applications, the primary concern is whether profitability can be improved, and the time horizon of interest is short-term. The technical details of the modeling process and "proof" of model validity in a scientific sense may not be important. In medical research, on the other hand, the consequences of flawed analysis can be very serious. Patients might be harmed either by being exposed to an unsafe intervention or by failing to receive the optimal treatment. Because of the seriousness of these consequences, statistical analyses are subjected to much more severe scrutiny both internally and externally.

To test a new treatment, a randomized clinical trial (RCT) must be designed to be conducted rigorously and rigidly. A study protocol is written to specify, in advance, how the drugs will be administered, the data collected, and the statistical analyses performed. In an RCT, no material deviations from the protocol's requirements are tolerated.

Cadit-based methods could add value at all stages of the drug discovery process. Prior to the RCT, a set of potential predictor variables could be specified. A cadit regression model that incorporated these variables could be included in the study's protocol as a planned analysis. Running such a cadit regression could provide a useful test of whether personalization based on any of these variables (or on any combination of these variables) would be possible.

During the study, interim analyses could be performed under the auspices of a special "discovery team" that might be connected to the study's Data Monitoring Committee. This team's function would be to identify possible causal modifiers. After the study, it would still be possible to conduct exploratory analyses based on emerging biomedical knowledge. The data from an RCT could then continue to pay dividends as a valuable resource long after the study's original data collection is over. For example, by maintaining a bio-bank for all subjects, new promising genomic factors could be tested.

In an RCT analyzed using cadit-based methods, the predictor variables could be better linked to a causal effect. In particular, predictor variables that are statistically associated with participants that are either "Immune" or "Doomed" would have little to no effect on the ECE. Variables associated with being a "Causal" would have a positive relationship with the ECE, and variables associated with being a "Preventive" would have a negative relationship with the ECE. Therefore, individuals with a lower expectation of the cadit variable may be more likely to benefit from the treatment and/or less likely to be harmed by the treatment. In some cases, the sign of the cadit variable may be reversed, so that beneficial treatment would be associated with positive values of the cadit variable.

As a particular implementation, a software program may be provided to facilitate recommending medical treatment to particular individuals. Such a software program may receive, as an input, study data from an RCT, along with demographic or other characteristic data for the participants in the RCT. The software may then perform the process steps shown in FIG. 2 to generate an algorithm that uses the characteristic data to distinguish between patients that are more likely to be benefited by the treatment and patients that are less likely to be benefited by the treatment. The software may then cause the system to send or display, as an output, the generated algorithm or the recommendation(s) that result from using the algorithm to evaluate one or more patients. If the medical treatment is administered by an automated device, then the software may also cause the automated device to administer the treatment automatically to a set of patients that were chosen according to their ECE values. An example software program may also output both treatment recommendations and automatic treatment instructions. For example, the software may send treatment recommendations for patients with low values of ECE, while causing automatic treatments to be administered to patients with very low values of ECE.

The two example applications are only exemplary to illustrate how methods and systems may be applied to particular problems. Numerous other example situations may also be used.

VI. Conclusion

The construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited.

Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present disclosure. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the scope of the appended claims.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

What is claimed is:

1. A computer-implemented method comprising:
   receiving study data from a comparative study, wherein the study data are indicative of observed values of (i) exposure status, (ii) outcome, and (iii) one or more predictor variables, wherein each observed value is for a participant in the comparative study;
   calculating, for each respective participant in a set of participants in the study, a respective value of a causality variable, wherein the causality variable is a function of the observed values of exposure status and outcome for the respective participant, wherein an expectation of the causality variable for the respective participant is a monotone function of an individual causal effect (ICE) for the respective participant, and wherein the causality variable is a cadit variable defined as: cadit=T×R+(1−T)×(1−R), where T is exposure status defined as T=1 for a first treatment and T=0 for a second treatment and R is an outcome value;
   analyzing part of the study data to estimate a statistical relationship between the causality variable and the one or more predictor variables; and
   based at least in part on the estimated statistical relationship, generating an algorithm for distinguishing between individuals in accordance with values of the expectation of the causality variable for the individuals, wherein the algorithm uses values of the one or more predictor variables to distinguish between the individuals.

2. The method of claim 1,
   wherein each observed value of the outcome is one of a first outcome and a second outcome,
   wherein the causality variable is a high value for participants having a first exposure status and the first outcome, and
   wherein the causality variable is a low value for participants having a second exposure status and the first outcome,
   wherein the causality variable is a low value for participants having the first exposure status and the second outcome, and
   wherein the causality variable is a high value for participants having the second exposure status and the second outcome.

3. The method of claim 2, wherein the part of the study data is analyzed using logistic regression analysis.

4. The method of claim 1, further comprising dividing the set of participants in the study into subgroups according to their respective estimated expectations of the causality variable, wherein each subgroup is associated with a respective range of values of the expectation of the causality variable.

5. The method of claim 4, further comprising outputting a recommended treatment for each of the subgroups based on the respective range associated with the subgroup.

6. The method of claim 1, further comprising selecting an analytic subset of participants from the set of participants in the study, wherein the analytic subset includes an equalized number of participants from each of at least two study groups, and wherein each study group consists of participants that are associated with equivalent values of exposure status.

7. The method of claim 1, further comprising:
   receiving second data indicative of values of the one or more predictor variables for a set of individuals;
   using the generated algorithm to estimate a respective expectation of the causality variable for each individual in the second set of individuals; and
   ranking the second set of individuals according to the estimated respective expectation of the causality variable for each individual.

8. The method of claim 1, further comprising:
   receiving second data indicative of values of the one or more predictor variables for a set of individuals;
   using the generated algorithm to estimate a respective expectation of the causality variable for each individual in the second set of individuals; and
   dividing the second set of individuals into subgroups according to the estimated expectations of the causality variable, wherein each subgroup is associated with a respective range of values of the estimated expectation of the causality variable.

9. The method of claim 1, further comprising outputting the generated algorithm in the form of a computer-readable medium.

10. The method of claim 1, further comprising using an inverse of the monotone function to estimate a value of the ICE for one or more individuals, based on values of the one or more predictor variables.

11. A computer-implemented method for testing a statistical significance of one or more predictor variables for facilitating prediction of a value of an individualized causal effect (ICE), the method comprising:
receiving study data from a comparative study, wherein the study data is indicative of observed values of (i) exposure status, (ii) outcome, and (iii) one or more predictor variables, calculating, for each respective participant in a set of participants in the study, a respective value of a causality variable, wherein the causality variable is a function of the observed values of exposure status and outcome for the respective participant, wherein an expectation of the causality variable for the respective participant is a monotone function of the ICE for the respective participant, and wherein the causality variable is a cadit variable defined as: $cadit = T \times R + (1-T) \times (1-R)$, where T is exposure status defined as T=1 for a first treatment and T=0 for a second treatment and R is an outcome value;
wherein each observed value is for a participant in the comparative study;
calculating, for each respective participant in a set of participants in the study, a respective value of a causality variable, wherein the causality variable is a function of the observed values of exposure status and outcome for the respective participant, and wherein an expectation of the causality variable for the respective participant is a monotone function of the ICE for the respective participant;
performing a statistical analysis on at least part of the study data, wherein the statistical analysis is performed using the causality variable as a dependent variable and at least the one or more predictor variables as independent variables; and
based on the performed statistical analysis, determining the statistical significance of a relationship between the one or more predictor variables and the causality variable.

12. The method of claim 11, wherein the statistical significance of a group of two or more of the predictor variables is determined on a group basis.

13. The method of claim 11, further comprising:
identifying at least one significant predictor variable based on the determined statistical significance of the one or more predictor variables; and
generating an algorithm relating the at least one significant predictor variable to the expectation of the causality variable.

14. The method of claim 11,
wherein each observed value of outcome is one of a first outcome and a second outcome,
wherein the causality variable is a high value for participants having a first exposure status and the first outcome, and
wherein the causality variable is a low value for participants having a second exposure status and the first outcome,
wherein the causality variable is a low value for participants having the first exposure status and the second outcome, and
wherein the causality variable is a high value for participants having the second exposure status and the second outcome.

15. The method of claim 14, wherein at least the part of the study data is analyzed using logistic regression analysis.

16. A non-transitory computer-readable medium having stored thereon program instructions executable by a processor to cause the processor to perform functions comprising:
receiving study data from a comparative study, wherein the study data is indicative of observed values of (i) exposure status, (ii) outcome, and (iii) the one or more predictor variables, wherein each observed value is for a participant in the comparative study;
calculating, for each respective participant in a set of participants in the study, a respective value of a causality variable that is a function of the observed values of exposure status and outcome for the respective participant, wherein an expectation of the causality variable for the respective participant is a monotone function of an individual causal effect (ICE) for the respective participant, and wherein the causality variable is a cadit variable defined as: $cadit = T \times R + (1-T) \times (1-R)$, where T is exposure status defined as T=1 for a first treatment and T=0 for a second treatment and R is an outcome value;
analyzing part of the study data to estimate a statistical relationship between the causality variable and the one or more predictor variables; and
based at least in part on the estimated statistical relationship, generating an algorithm for distinguishing between individuals in accordance with values of the expectation of the causality variable for the individuals, wherein the algorithm uses values of the one or more predictor variables to distinguish between the individuals.

17. The computer-readable medium of claim 16, wherein the program instructions are further executable by a processor to cause the processor to:
receive second data indicative of values of the one or more predictor variables for a set of individuals;
use the generated algorithm to determine a respective expectation of the causality variable for each individual in the second set of individuals; and
divide the second set of individuals into subgroups according to the respective expectation of the causality variable, wherein each subgroup is associated with a respective range of values of the expectation of the causality variable.

18. The computer-readable medium of claim 16, the functions further comprising outputting the generated algorithm in the form of a second computer-readable medium.

19. A computer-implemented method comprising:
receiving study data from a comparative study, wherein the study data are indicative of observed values of (i) exposure status, (ii) outcome, and (iii) one or more predictor variables, wherein each observed value is for a participant in the comparative study;
calculating, for each respective participant in a set of participants in the study, a respective value of a causality variable, wherein the causality variable is a function of the observed values of exposure status and outcome for the respective participant, wherein an expectation of the causality variable for the respective participant is a monotone function of an individual causal effect (ICE) for the respective participant, and wherein the causality variable is a cadit variable, $Z_i$, defined for each individual, i, as:

$$Z_i = \frac{Y_i - \overline{Y}}{2t(1-t)}$$

if individual i received a first treatment, and $$Z_i = \frac{-(Y_i - \overline{Y})}{2t(1-t)}$$

individual i received a second treatment,
wherein Yi is an observed value of outcome for individual i and $\overline{Y}$ is a mean of one or more observed values of outcome from the comparative study, and wherein t is a proportion of the participants that received the first treatment;

analyzing part of the study data to estimate a statistical relationship between the causality variable and the one or more predictor variables; and based at least in part on the estimated statistical relationship, generating an algorithm for distinguishing between individuals in accordance with values of the expectation of the causality variable for the individuals, wherein the algorithm uses values of the one or more predictor variables to distinguish between the individuals.

20. A computer-implemented method for testing a statistical significance of one or more predictor variables for facilitating prediction of a value of an individualized causal effect (ICE), the method comprising:

receiving study data from a comparative study, wherein the study data is indicative of observed values of (i) exposure status, (ii) outcome, and (iii) one or more predictor variables, wherein each observed value is for a participant in the comparative study;

calculating, for each respective participant in a set of participants in the study, a respective value of a causality variable, wherein the causality variable is a function of the observed values of exposure status and outcome for the respective participant, wherein an expectation of the causality variable for the respective participant is a monotone function of the ICE for the respective participant, and wherein the causality variable is a cadit variable, $Z_i$, defined for each individual, i, as:

$$Z_i = \frac{Y_i - \overline{Y}}{2t(1-t)}$$

if individual i received a first treatment, and $$Z_i = \frac{-(Y_i - \overline{Y})}{2t(1-t)}$$

individual i received a second treatment,
wherein Yi is an observed value of outcome for individual i and $\overline{Y}$ is a mean of one or more observed values of outcome from the comparative study, and wherein t is a proportion of the participants that received the first treatment;

performing a statistical analysis on at least part of the study data, wherein the statistical analysis is performed using the causality variable as a dependent variable and at least the one or more predictor variables as independent variables; and based on the performed statistical analysis, determining the statistical significance of a relationship between the one or more predictor variables and the causality variable.

21. A non-transitory computer-readable medium having stored thereon program instructions executable by a processor to cause the processor to perform functions comprising:

receiving study data from a comparative study, wherein the study data is indicative of observed values of (i) exposure status, (ii) outcome, and (iii) the one or more predictor variables, wherein each observed value is for a participant in the comparative study;

calculating, for each respective participant in a set of participants in the study, a respective value of a causality variable that is a function of the observed values of exposure status and outcome for the respective participant, wherein an expectation of the causality variable for the respective participant is a monotone function of an individual causal effect (ICE) for the respective participant, and wherein the causality variable is a cadit variable, $Z_i$, defined for each individual, i, as:

$$Z_i = \frac{Y_i - \overline{Y}}{2t(1-t)}$$

if individual i received a first treatment, and $$Z_i = \frac{-(Y_i - \overline{Y})}{2t(1-t)}$$

individual i received a second treatment,
wherein Yi is an observed value of outcome for individual i and $\overline{Y}$ is a mean of one or more observed values of outcome from the comparative study, and wherein t is a proportion of the participants that received the first treatment;

analyzing part of the study data to estimate a statistical relationship between the causality variable and the one or more predictor variables; and based at least in part on the estimated statistical relationship, generating an algorithm for distinguishing between individuals in accordance with values of the expectation of the causality variable for the individuals, wherein the algorithm uses values of the one or more predictor variables to distinguish between the individuals.

22. The method of claim 19,
wherein the observed values of the outcome are continuous,
wherein the causality variable is a monotonically increasing function of the observed value of the outcome for each participant having a first exposure status, and
wherein the causality variable is a monotonically decreasing function of the observed value of the outcome for each participant having a second exposure status.

23. The method of claim 20,
wherein the observed values of the outcome are continuous,
wherein the causality variable is a monotonically increasing function of the observed values of the outcome for participants having a first exposure status, and
wherein the causality variable is a monotonically decreasing function of the observed values of the outcome for participants having a second exposure status.

* * * * *

UNITED STATES PATENT AND TRADEMARK OFFICE
CERTIFICATE OF CORRECTION

PATENT NO. : 8,688,610 B1
APPLICATION NO. : 13/675597
DATED : April 1, 2014
INVENTOR(S) : Herbert I. Weisberg and Victor P. Pontes Page 1 of 1

It is certified that error appears in the above-identified patent and that said Letters Patent is hereby corrected as shown below:

IN THE CLAIMS

In column 24, line 29, in claim 3, please replace "claim 2" with -- claim 1 --

Signed and Sealed this
Twenty-first Day of October, 2014

Michelle K. Lee
*Deputy Director of the United States Patent and Trademark Office*